US012758525B2

(12) United States Patent
Palte et al.

(10) Patent No.: US 12,758,525 B2
(45) Date of Patent: Oct. 13, 2026

(54) COMBINATION TREATMENT METHODS OF MULTIPLE SCLEROSIS

(71) Applicant: BIOGEN MA INC., Cambridge, MA (US)

(72) Inventors: Michael Joseph Palte, Melrose, MA (US); Brian T. Hopkins, Newton, MA (US); Matthew P. Scaramozza, West Roxbury, MA (US); Michael Christian Mingueneau, Somerville, MA (US); Alex Pellerin, Dorchester, MA (US); Chelsea R. Parker Harp, Boston, MA (US); Catherine Barbey, Lausanne (CH)

(73) Assignee: BIOGEN MA INC., Cambridge, MA (US)

( * ) Notice: Subject to any disclaimer, the term of this patent is extended or adjusted under 35 U.S.C. 154(b) by 426 days.

(21) Appl. No.: 18/285,123

(22) PCT Filed: Apr. 1, 2022

(86) PCT No.: PCT/US2022/023132
§ 371 (c)(1),
(2) Date: Sep. 29, 2023

(87) PCT Pub. No.: WO2022/212893
PCT Pub. Date: Oct. 6, 2022

(65) Prior Publication Data
US 2024/0216330 A1 Jul. 4, 2024

Related U.S. Application Data

(60) Provisional application No. 63/170,048, filed on Apr. 2, 2021.

(51) Int. Cl.

| | |
|---|---|
| ***A61K 31/4015*** | (2006.01) |
| ***A61K 31/225*** | (2006.01) |
| ***A61K 31/4545*** | (2006.01) |
| ***A61K 31/4985*** | (2006.01) |
| ***A61K 31/506*** | (2006.01) |
| ***A61P 25/28*** | (2006.01) |
| ***A61P 37/00*** | (2006.01) |

(52) U.S. Cl.
CPC ........ *A61K 31/4015* (2013.01); *A61K 31/225* (2013.01); *A61K 31/4545* (2013.01); *A61K 31/4985* (2013.01); *A61K 31/506* (2013.01); *A61P 25/28* (2018.01); *A61P 37/00* (2018.01)

(58) Field of Classification Search
CPC ............ A61K 31/4015; A61K 31/4192; A61K 31/215; A61K 31/225; A61K 31/4545; A61K 31/4985; A61K 31/506; A61P 37/00
See application file for complete search history.

(56) References Cited

U.S. PATENT DOCUMENTS

| | | | | |
|---|---|---|---|---|
| 7,619,001 B2 * | 11/2009 | Joshi | ...................... A61P 37/02 514/960 |
| 9,809,577 B2 | 11/2017 | Hopkins et al. | |
| 10,081,619 B2 | 9/2018 | Hopkins et al. | |
| 10,189,829 B2 | 1/2019 | Hopkins et al. | |
| 10,227,341 B2 | 3/2019 | Hopkins et al. | |
| 10,759,783 B2 | 9/2020 | Hopkins et al. | |
| 10,961,237 B2 | 3/2021 | Hopkins et al. | |
| 11,427,577 B2 | 8/2022 | Hopkins et al. | |
| 11,572,356 B2 | 2/2023 | Hopkins et al. | |
| 11,858,926 B2 | 1/2024 | Hopkins et al. | |
| 2018/0297992 A1 | 10/2018 | Hopkins et al. | |

FOREIGN PATENT DOCUMENTS

| | | | |
|---|---|---|---|
| WO | WO-2013067274 A1 * | 5/2013 | .............. A61P 37/00 |
| WO | 2015/028472 A1 | 3/2015 | |
| WO | WO-2015048662 A2 * | 4/2015 | .............. A61P 43/00 |
| WO | 2015/086467 A1 | 6/2015 | |
| WO | WO-2016196840 A1 * | 12/2016 | ........... C07D 476/34 |
| WO | WO-2018191577 A1 * | 10/2018 | ................ A61P 1/16 |
| WO | 2020/055698 A1 | 3/2020 | |

OTHER PUBLICATIONS

Derfuss et al., “Advances in oral immunomodulating therapies in relapsing multiple sclerosis”, Lancet Neurology, vol. 19, No. 4, pp. 336-347 (2020).*
Montalban et al., Placebo-Controlled Trial of an Oral BTK Inhibitor in Multiple Sclerosis. N Engl J Med. Jun. 20, 2019;380(25):2406-2417.
International Search Report and Written Opinion for Application No. PCT/US2022/023132, dated Jun. 22, 2022, 10 pages.
International Preliminary Report on Patentability for Application No. PCT/US2022/023132, dated Oct. 12, 2023, 7 pages.
U.S. Appl. No. 15/103,749, filed Jun. 10, 2016, U.S. Pat. No. 9,809,577, Issued.
U.S. Appl. No. 15/651,788, filed Jul. 17, 2017, Abandoned.
U.S. Appl. No. 15/699,857, filed Sep. 8, 2017, U.S. Pat. No. 10,081,619, Issued.
U.S. Appl. No. 16/108,755, filed Aug. 22, 2018, U.S. Pat. No. 10,759,783, Issued.
U.S. Appl. No. 17/004,411, filed Aug. 27, 2020, U.S. Pat. No. 11,572,356, Issued.
U.S. Appl. No. 18/104,845, filed Feb. 2, 2023, Abandoned.

(Continued)

*Primary Examiner* — Kevin E Weddington
(74) *Attorney, Agent, or Firm* — McCarter & English, LLP; Xin Zhang

(57) ABSTRACT

The present disclosure provides combination therapies for treating an autoimmune disease in a subject in need thereof. The methods comprise administering to the subject an effective amount of a BTK inhibitor in combination with an effective amount of a fumaric acid ester (FAE). The autoimmune disease can be treated include, for example, multiple sclerosis (MS), lupus, rheumatoid arthritis (RA), Pemphigus Vugaris (PV), neuromyelitis optica (NMO), myasthenia gravis (MG), chronic inflammatory demyelinating polyneuropathy (CIDP), anti-NMDA receptor encephalitis, or Sjogren’s disease.

9 Claims, 5 Drawing Sheets

(56) References Cited

OTHER PUBLICATIONS

U.S. Appl. No. 18/217,720, filed Jul. 3, 2023, Abandoned.
U.S. Appl. No. 18/523,245, filed Nov. 29, 2023, Abandoned.
U.S. Appl. No. 18/634,431, filed Apr. 12, 2024, Pending.
U.S. Appl. No. 18/815,186, filed Aug. 26, 2024, Pending.
U.S. Appl. No. 15/952,505, filed Apr. 13, 2018, U.S. Pat. No. 10,227,341, Issued.
U.S. Appl. No. 16/113,455, filed Aug. 27, 2018, U.S. Pat. No. 10,189,829, Issued.
U.S. Appl. No. 16/246,986, filed Jan. 14, 2019, Abandoned.
U.S. Appl. No. 16/534,540, filed Aug. 7, 2019, U.S. Pat. No. 10,961,237, Issued.
U.S. Appl. No. 17/183,702, filed Feb. 24, 2021, U.S. Pat. No. 11,427,577, Issued.
U.S. Appl. No. 17/871,157, filed Jul. 22, 2022, U.S. Pat. No. 11,858,926, Issued.
U.S. Appl. No. 18/510,242, filed Nov. 15, 2023, Abandoned.
U.S. Appl. No. 18/620,238, filed Mar. 28, 2024, Pending.
U.S. Appl. No. 18/798,212, filed Aug. 8, 2024, Pending.
Dolgin et al., BTK blockers make headway in multiple sclerosis. Nat Biotechnol. Jan. 2021;39(1):3-5.

* cited by examiner

COMBINATION TREATMENT METHODS OF MULTIPLE SCLEROSIS

RELATED APPLICATIONS

This application is a 35 U.S.C. § 371 national stage filing of International Application No. PCT/US2022/023132, filed on Apr. 1, 2022, which in turn claims the benefit of the filing date, under 35 U.S.C. § 119(e), of U.S. Provisional Application No. 63/170,048, filed on Apr. 2, 2021. The entire contents of each of the foregoing applications are incorporated herein by reference.

BACKGROUND

Multiple sclerosis (MS) is a chronic, autoimmune, demyelinating disorder of the central nervous system (CNS) that is characterized by inflammation, demyelination, and axonal injury as well as oligodendrocyte and neuronal loss. It is the most common demyelinating disorder of the CNS, affecting approximately 2.5 million people worldwide. Relapsing multiple sclerosis (RMS) includes patients with clinically isolated syndrome (CIS), relapsing-remitting multiple sclerosis (RRMS), and active secondary progressive multiple sclerosis (SPMS). In the relapsing-remitting phase of the disease, patients experience episodes of neurological dysfunction (relapses) separated by periods of relative stability. Other types of MS include primary progressive multiple sclerosis (PPMS) and non-relapsing SPMS. Patients with radiologically isolated syndrome (RIS) may go on to develop MS.

While there has been substantial progress in MS care over the last 25 years with the approval of a number of medicinal products, many patients with MS continue to experience permanent disability progression, and many receive therapies with limited tolerability, burdensome monitoring, or risk of severe adverse events (SAEs) or even life-threatening side effects. There remains an important unmet need for tolerable MS therapies that are highly efficacious and include new options for treating the inflammatory component of MS seen across the spectrum of RMS through progressive multiple sclerosis (PMS) types, as well as effectively treating disability progression independent of relapse activity.

SUMMARY OF THE INVENTION

The present disclosure provides methods of treating an autoimmune disease (e.g., MS) in a subject in need thereof comprising administering to the subject an effective amount of a BTK inhibitor and an effective amount of a fumaric acid ester (FAE).

The present disclosure also provides use of a BTK inhibitor for the manufacture of a medicament for treating an autoimmune disease (e.g., MS) in a subject in need thereof, in combination with a FAE.

Also included in the present disclosure is a BTK inhibitor for use in a method of treating an autoimmune disease (e.g. MS) in a subject in need thereof, in combination with a FAE.

DETAILED DESCRIPTION OF THE INVENTION

Figure 1:
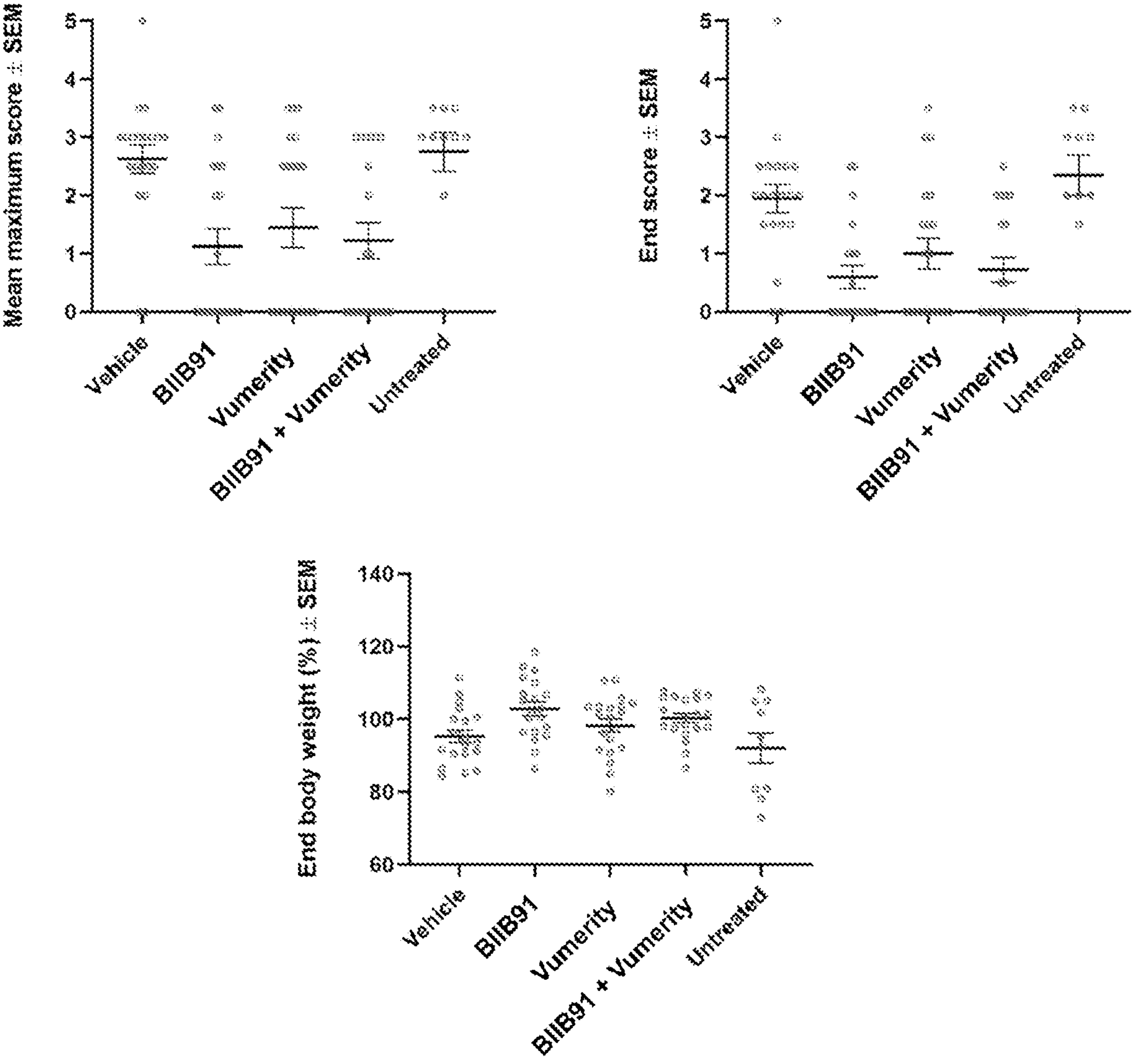
FIG. 1 shows mean maximum score, end score and end body weight for each treatment group in the in vivo murine model of multiple sclerosis.

The present disclosure provides combination therapies for treating an autoimmune disease (e.g., MS) in a subject in need thereof. The methods comprise administering to the subject an effective amount of a BTK inhibitor in combination with an effective amount of a fumaric acid ester (FAE). In some embodiments, a lower dose of a FAE (compared to the monotherapy dose) can be used to achieve maximum efficacy when dosed in combination with a BTK inhibitor, exhibiting a synergistic effect with the BTK inhibitor. In some embodiments, a lower dose of a BTK inhibitor (compared to the monotherapy dose) can be used to achieve maximum efficacy when dosed in combination with a FAE, exhibiting a synergistic effect with the BTK inhibitor.

BTK Inhibitors

Bruton's tyrosine kinase (BTK), a member of the tyrosine kinase hepatocellular carcinoma (TEC) family of protein tyrosine kinases, is expressed in many hematopoietic cell types known to be dysregulated in MS. Additionally, pathogenic activation of B cells is considered a key driver in the maintenance of active inflammation in MS. Recent studies in patients with MS have established B cells as a clinically validated target cell type in MS. In addition to B cells, there is a body of support for the pathological role of myeloid cells (monocytes, macrophages, dendritic cells, mast cells, and granulocytes) in MS. BTK is a key signaling node immediately downstream of the B-cell receptor (BCR) in B cells and Fc receptors (FcRs) in myeloid cells. In B cells, BTK mediates B-cell activation and effector functions (such as cytokine secretion and proliferation and differentiation into memory cells and antibody-producing cells) downstream of BCR activation and is required for BCR-mediated antigen presentation to T cells. In myeloid cells, BTK inhibition blocks FcR dependent pro-inflammatory activities (including cytokine secretion by mast cells, monocytes, and macrophages; reactive oxygen species generation by neutrophils; and degranulation of basophils) triggered by binding of immune complexes to FcRs. Genetic ablation of all activating FcγRs or FcγRIII has established the pathogenic role of FcRs in myeloid cells in MS nonclinical models. The role of FcRs in disease pathogenesis is not completely understood but includes immune complex mediated endocytosis and antigen presentation to T cells as well as the regulation of myeloid cell activation and functions. Therefore, by targeting both B cells and myeloid cells, BTK inhibitors have the potential to offer additional clinical benefits as compared to therapies targeting only B cells.

Any suitable BTK inhibitors known in the art can be used in the methods described herein. As used herein, a suitable BTK inhibitor is a BTK inhibitor that has minimal drug-drug interactions when used in combination with FAEs and/or has minimally overlapping toxicities with the FAEs. In some embodiments, the BTK inhibitors suitable for use in the present methods do not have detrimental effects on liver enzymes. In some embodiments, the BTK inhibitors are selective BTK inhibitors. In other embodiments, the BTK inhibitors are reversible BTK inhibitors. In other embodiments, the BTK inhibitors can be irreversible covalent BTK inhibitors.

In some embodiments, the BTK inhibitor is selected from those described in WO 2015/089337, WO 2015/089327, WO 2018/191577, WO 2011/029043, WO 2012/058645, WO 2013/185082, and WO 2019/222101, each of which are incorporated herein by reference in their entireties.

In some embodiments, exemplary BTK inhibitors include, but are not limited to, ABBV-105 (AbbVie), AC-0058TA (ACEA Biosciences), acalabrutinib (4-[8-amino-3-[(2S)-1-but-2-ynoylpyrrolidin-2-yl]imidazo[1,5-a]pyrazin-1-yl]-N-pyridin-2-ylbenzamide, structure shown below, Acerta Pharma), AS-1763 (Carna Biosciences), AS-0871 (structure shown below, Carna Biosciences), BIIB-068 (structure shown below, Biogen), BIIB-091 (structure shown below, Biogen), BMS-986142 ((7S)-3-fluoro-4-[3-(8-fluoro-1-methyl-2,4-dioxoquinazolin-3-yl)-2-methylphenyl]-7-(2-hydroxypropan-2-yl)-6,7,8,9-tetrahydro-5H-carbazole-1-carboxamide, structure shown below, Bristol-Myers Squibb), branebrutinib (4-[(3S)-3-(but-2-ynoylamino)piperidin-1-yl]-5-fluoro-2,3-dimethyl-1H-indole-7-carboxamide, structure shown below, Bristol-Myers Squibb, see, e.g. WO 2014/210085 and BTK inhibitors described therein), Gossamer 161807. Shenogen 175719, CG-026806 (1-[3-fluoro-4-[7-(5-methyl-1H-imidazol-2-yl)-1-oxo-2,3-dihydroisoindol-4-yl]phenyl]-3-[3-(trifluoromethyl)phenyl]urea, structure shown below, CrystalGenomics, see, e.g. U.S. Pat. No. 9,758,608 and WO 2012/047017 and BTK inhibitors described therein), CG-100650 (CrystalGenomics), CLR-1700 series (Cellectar Biosciences), DTRMWXHS-12 (Zhejiang DTRM Biopharma), Curadev Pharma 122605 (Curadev Pharma), DWJ-212 (Daewoong), DWJ-213 (Daewoong), evobrutinib (1-[4-[[[6-amino-5-(4-phenoxyphenyl)pyrimidin-4-yl]amino]methyl]piperidin-1-yl]prop-2-en-1-one, structure shown below, Merck Serono, see, e.g., WO 2012/170976 and BTK inhibitors described herein), FCN-647 (Fochon Pharma), fencbrutinib (10-[3-(hydroxymethyl)-4-[1-methyl-5-[[5-[(2S)-2-methyl-4-(oxctan-3-yl)piperazin-1-yl]pyridin-2-yl]amino]-6-oxopyridin-3-yl]pyridin-2-yl]-4,4-dimethyl-1,10-diazatricyclo[6.4.0.02,6]dodeca-2(6), 7-dien-9-one, structure shown below, Roche, see, e.g., WO 2013/067274 and BTK inhibitors described therein), HWH-486 (Humanwell Healthcare), HZ-A-018 (Hangzhou Hertz Pharmaceutical), ibrutinib (1-[(3R)-3-[4-amino-3-(4-phenoxyphenyl)pyrazolo[3,4-d]pyrimidin-1-yl]piperidin-1-yl]prop-2-en-1-one, structure shown below, Pharmacylics), JNJ-64264681 (Johnson & Johnson), KBP-7536 (KBP Biosciences), LOU-064 (N-[3-[6-amino-5-[2-[methyl(prop-2-enoyl)amino]ethoxy]pyrimidin-4-yl]-5-fluoro-2-methylphenyl]-4-cyclopropyl-2-fluorobenzamide, structure shown below, Novartis, see, e.g., WO 2015/079417 and BTK inhibitor described therein), LOXO-305 (Eli Lilly), M-7583 (5-amino-N-ethyl-2-methyl-N-phenylbenzenesulfonamide, under development by Merck KGAA), MK-1026 (Arqule, see, e.g., U.S. Pat. No. 9,630,968 and BTK inhibitors described therein), orelabrutinib (2-(4-phenoxyphenyl)-6-(1-prop-2-enoylpiperidin-4-yl)pyridine-3-carboxamide, structure shown below, InnoCare, see, e.g., WO 2015/048662 and other BTK inhibitors described therein), poseltinib (N-[3-[2-[4-(4-methylpiperazin-1-yl)anilino]furo[3,2-d]pyrimidin-4-yl]oxyphenyl]prop-2-enamide, structure shown below, Hanmi, see, e.g., WO 2011/162515 and BTK inhibitors described therein), PRN-473 (Principia Biopharma), rilzabrutinib ((E)-2-[(3R)-3-[4-amino-3-(2-fluoro-4-phenoxyphenyl)pyrazolo[3,4-d]pyrimidin-1-yl]piperidine-1-carbonyl]-4-methyl-4-[4-(oxetan-3-yl)piperazin-1-yl]pent-2-enenitrile, structure shown below, Principia Biopharma, see, e.g., WO 2014039899 and BTK inhibitors described therein), tolebrutinib (4-amino-3-(4-phenoxyphenyl)-1-[(3R)-1-prop-2-enoylpiperidin-3-yl]imidazo[4,5-c]pyridin-2-one, also known as SAR-442168 or PRN-2246, structure shown below, Principia Biopharma, see, e.g., WO 2016/196840 and BTK inhibitors described therein), spebrutinib (N-[3-[[5-fluoro-2-[4-(2-methoxyethoxy)anilino]pyrimidin-4-yl]amino]phenyl]prop-2-enamide, structure shown below, Celgene, see, e.g., US20100249092, US20100029610, WO 2012/021444, US20130065899, US20130065879 and US20130072469 and BTK inhibitors described therein), SN1011 (SinoMab BioScience), TAK-020 (Ligand), TAS-5315 (Taiho), TG-1701 (Jiangsu Hengrui Medicine), tirabrutinib (6-amino-9-[(3R)-1-but-2-ynoylpyrrolidin-3-yl]-7-(4-phenoxyphenyl)purin-8-one, structure shown below, Ono Pharmaceutical, see, e.g., WO2011152351 and BTK inhibitors described therein), vecabrutinib ((3R,4S)-1-(6-amino-5-fluoropyrimidin-4-yl)-3-[(3R)-3-[3-chloro-5-(trifluoromethyl)anilino]-2-oxopiperidin-1-yl]piperidine-4-carboxamide, structure shown below, Sunesis, see, e.g., U.S. Pat. Nos. 8,785,440, 9,249,146, and 9,394,277, and WO 2013/185084 and BTK inhibitors described therein), XNW-1011 (Sinovent), zanubrutinib ((7S)-2-(4-phenoxyphenyl)-7-(1-prop-2-enoylpiperidin-4-yl)-4,5,6,7-tetrahydropyrazolo[1,5-a]pyrimidine-3-carboxamide, structure shown below, BeiGene), ZXBT-1055 (Guangzhou BeBetter Medicine), ZXBT-1158 (Guangzhou BeBetter Medicine), or a pharmaceutically acceptable salt any one of the aforementioned compounds.

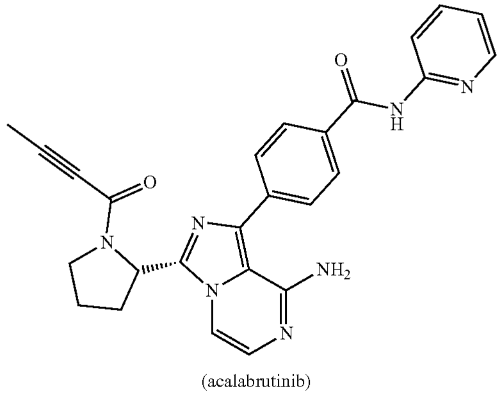
, (acalabrutinib)

-continued
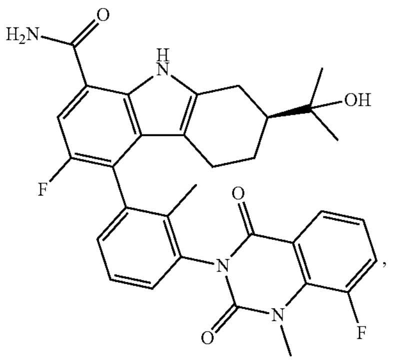
(BMS-986142)
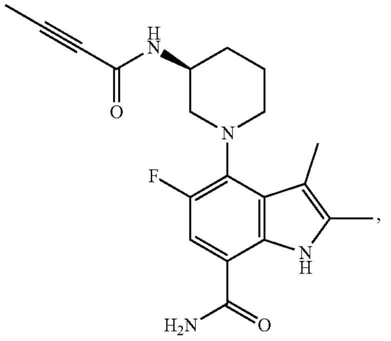
(branebrutinib)
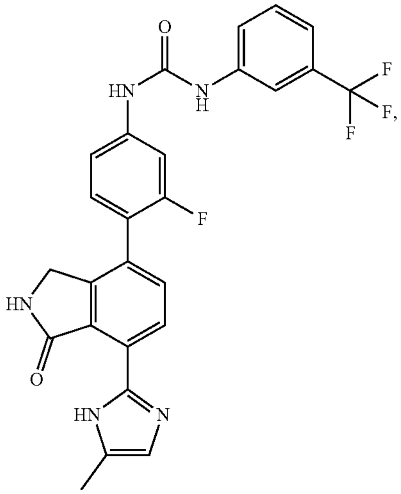
(CG-026806)
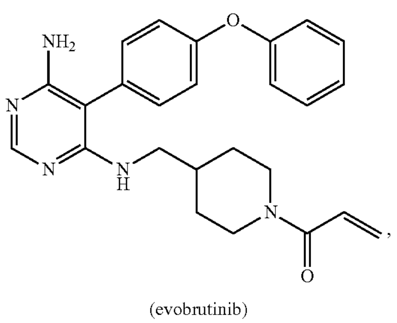
(evobrutinib)
-continued
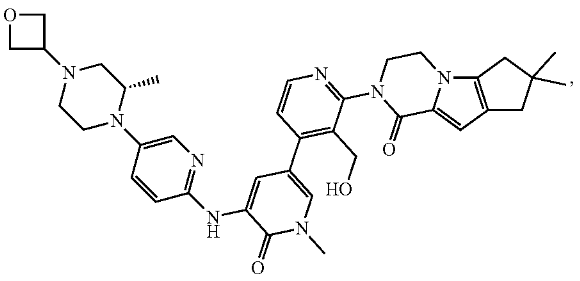
(fenebrutinib)
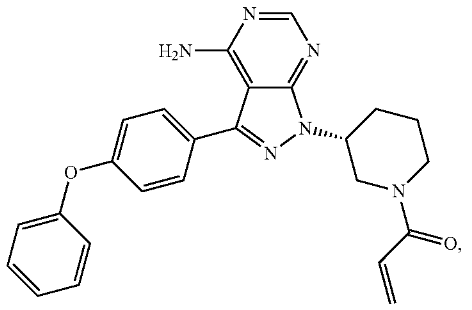
(ibrutinib)
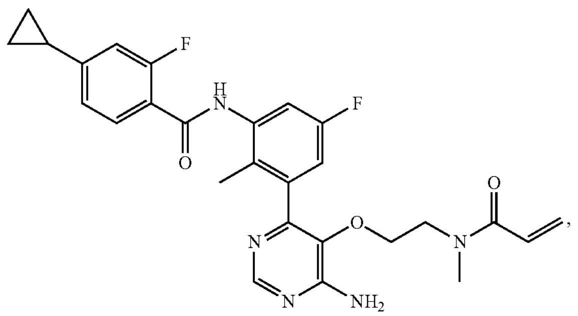
(LOU64)
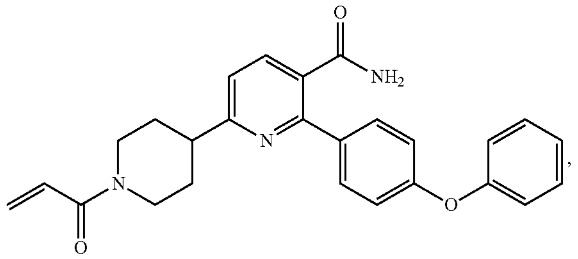
(orelabrutinib)
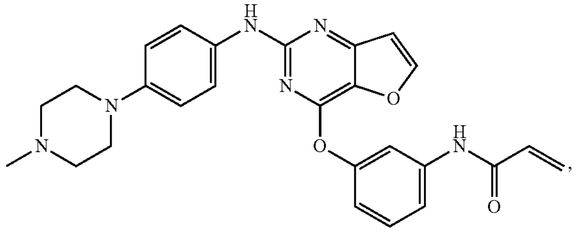
(poseltinib)

-continued
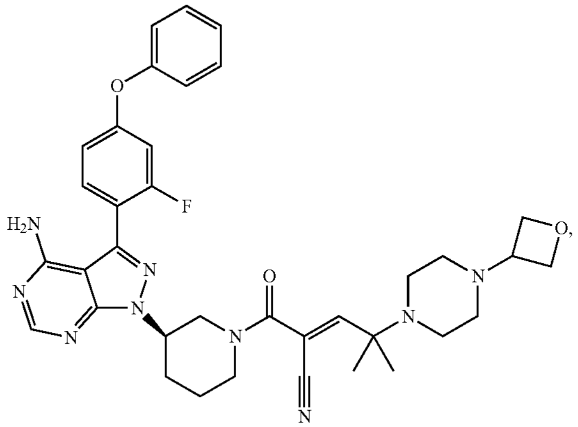
(rilzabrutinib)
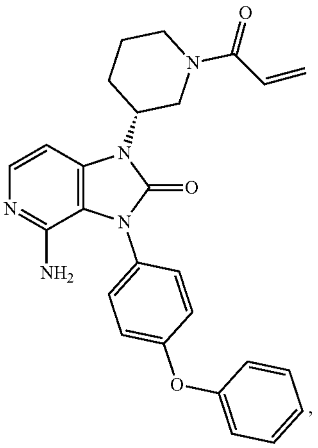
(tolebrutinib)
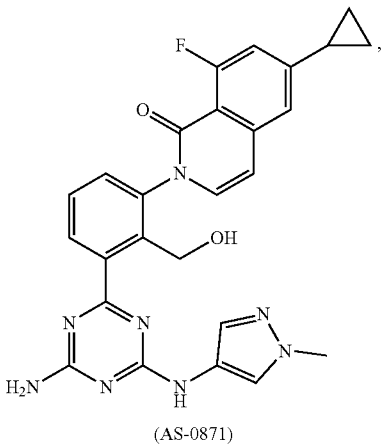
(AS-0871)
-continued
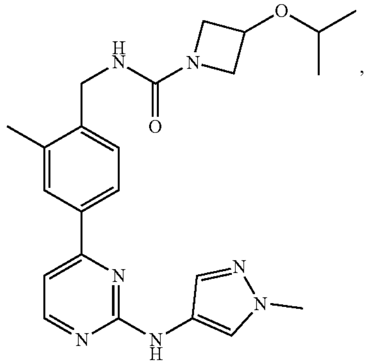
(BIIB068)
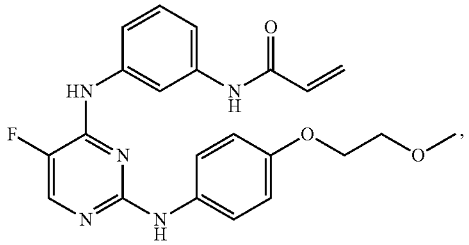
(spebrutinib)
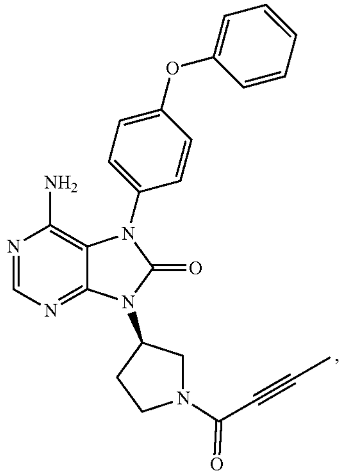
(tirabrutinib)
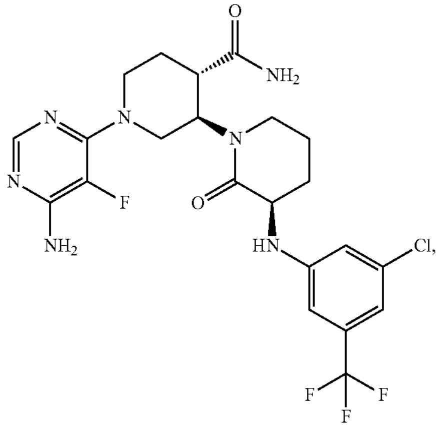
(vecabrutinib)

-continued

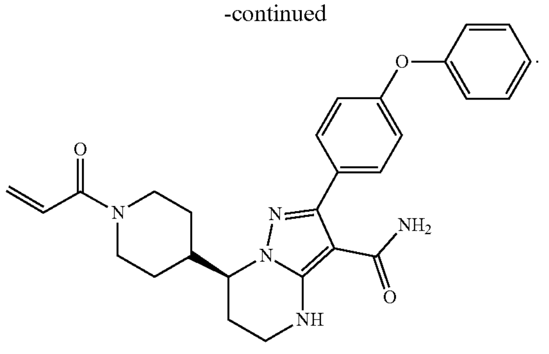

(zanubrutinib)

In some embodiments, the BTK inhibitor is (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide represented by the following structural formula:

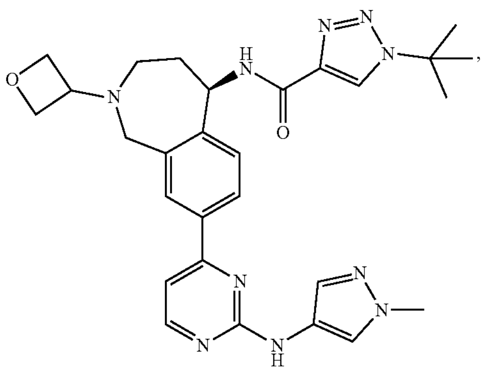

(BIIB-091)

or a pharmaceutically acceptable salt thereof.

In some embodiments, the BTK inhibitor is fenebrutinib (10-[3-(hydroxymethyl)-4-[1-methyl-5-[[5-[(2S)-2-methyl-4-(oxetan-3-yl)piperazin-1-yl]pyridin-2-yl]amino]-6-oxopyridin-3-yl]pyridin-2-yl]-4,4-dimethyl-1,10-diazatricyclo[6.4.0.02,6]dodeca-2(6),7-dien-9-one) represented by the following structural formula:

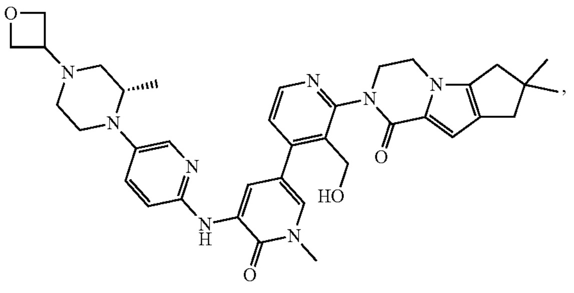 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1]

or a pharmaceutically acceptable salt thereof.

In some embodiments, the BTK inhibitor is branebrutinib (4-[(3S)-3-(but-2-ynoylamino)piperidin-1-yl]-5-fluoro-2,3-dimethyl-1H-indole-7-carboxamide) represented by the following structural formula:

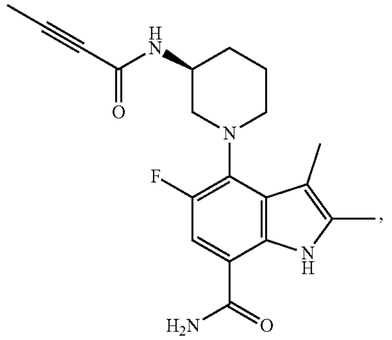 [SMILES: CC#CC(=O)N[C@H]1CCCN(c2c(F)cc(C(N)=O)c3[nH]c(C)c(C)c23)C1]

or a pharmaceutically acceptable salt thereof.

In some embodiments, the BTK inhibitor is evobrutinib (1-[4-[[[6-amino-5-(4-phenoxyphenyl)pyrimidin-4-yl]amino]methyl]piperidin-1-yl]prop-2-en-1-one) represented by the following structural formula:

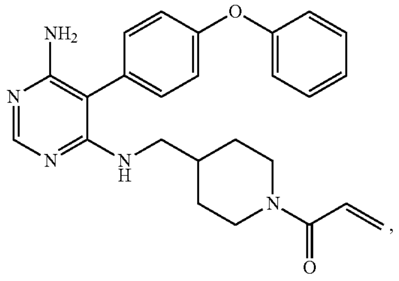 [SMILES: C=CC(=O)N1CCC(CNc2ncnc(N)c2-c2ccc(Oc3ccccc3)cc2)CC1]

or a pharmaceutically acceptable salt thereof.

In some embodiments, the BTK inhibitor is tolebrutinib (4-amino-1,3-dihydro-1-((3R)-1-(1-oxo-2-propen-1-yl)-3-piperidinyl)-3-(4-phenoxyphenyl)-2H-imidazo(4,5-c)pyridin-2-one, also known as SAR442168 and PRN-2246) represented by the following structural formula:

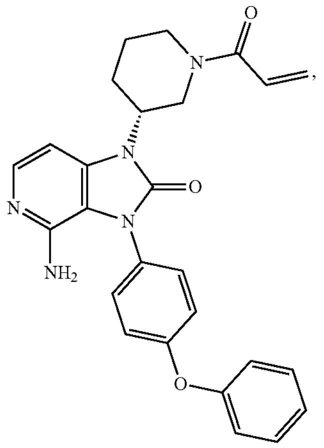 [SMILES: C=CC(=O)N1CCC[C@@H](n2c(=O)n(-c3ccc(Oc4ccccc4)cc3)c3c(N)nccc32)C1]

or a pharmaceutically acceptable salt thereof.

In some embodiments, the BTK inhibitor is orelabrutinib (2-(4-phenoxyphenyl)-6-(1-prop-2-enoylpiperidin-4-yl)pyridine-3-carboxamide represented by the following structural formula:

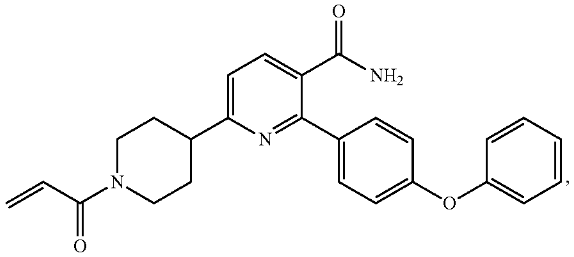 [SMILES: C=CC(=O)N1CCC(c2ccc(C(N)=O)c(-c3ccc(Oc4ccccc4)cc3)n2)CC1]

or a pharmaceutically acceptable salt thereof.

Fumaric Acid Esters (FAEs)

Fumaric acid esters, for example, are monomethyl fumarate (MMF) or prodrugs thereof. The term "MMF" refers to the compound, a pharmaceutically acceptable salt, or an ionized form of monomethyl fumarate. As used herein, a prodrug of MMF is a compound that can be metabolized into MMF in vivo.

MMF and its prodrugs, such as dimethyl fumarate (DMF) or diroximel fumarate (DRF), are a key class of therapeutics for the treatment of MS and primarily have immunomodulatory effects on the T-cell compartment as well as minimal impact on the B-cell compartment. An oral form of DMF, has been approved by the United States Food and Drug Administration since 2013 under the trade name Tecfidera® for the treatment of patients with relapsing forms of MS. Tecfidera® is available as hard gelatin delayed-release capsules containing 120 mg or 240 mg of dimethyl fumarate. The starting dose for Tecfidera® is 120 mg twice a day orally. After 7 days, the dose should be increased to the maintenance dose of 240 mg twice a day orally.

In some embodiments, the fumaric acid ester used in the methods of the present invention is MMF. In other embodiments, the fumaric acid ester is DMF. In yet other embodiments, a combination of MMF and DMF can be used in the methods described herein.

In some embodiments, the FAE in the methods of the present disclosure is DRF. DRF (also known as Vumerity®, BIIB098, ALKS 8700) is an oral di-ester fumarate treatment that has been approved by the US Food and Drug Administration for patients with relapsing forms of MS. Vumerity® is provided as hard, delayed-release capsules for oral administration. Each capsule contains 231 mg of diroximel fumarate. The starting dosage for Vumerity® is 231 mg twice a day orally. After 7 days, the dosage should be increased to the maintenance dosage of 462 mg twice a day orally. After oral administration, DRF undergoes rapid presystemic hydrolysis to produce the major active metabolite MMF (the same major metabolite as for DMF) as well as a major inactive metabolite 2-hydroxyethyl succinimide (HES) and a minor metabolite RDC-8439 (Palte, M J et al "Improving the Gastrointestinal Tolocrability of Fumaric Acid Esters: Early Findings on Gastrointestinal Events with Diroximel Fumarate in Patients with Relapsing-Remitting Multiple Sclerosis from the Phase 3, Open-Label EVOLVE-MS-1 Study" Adv Ther (2019) 36:3154-3165). The DRF 462 mg dose taken orally provides MMF exposure comparable to that of the DMF 240 mg dose taken orally; therefore, the efficacy and safety profile of the DRF 462 mg dose is expected to be similar to that of the DMF 240 mg. However, DRF has improved GI tolerability compared to DMF.

In some embodiments, the FAE that can be used in the methods of the present disclosure is Baficrtam™. Bafiertam™, delayed-release capsules containing 95 mg of MMF, has been recently approved by the US Food and Drug Administration for the treatment of relapsing forms of MS. The starting dose for Bafiertam™ is 95 mg twice a day orally for 7 days. After 7 days, the dosage should be increased to the maintenance dosage of 190 mg (administered as two 95 mg capsules) twice a day orally.

In some embodiments, the FAE in the methods of the present disclosure is XP-23839 (tepilamide fumarate, PCC-06, or 4-O-[2-(diethylamino)-2-oxocthyl] 1-O-methyl (E)-but-2-enedioate). XP-23839 was developed by Xenoport and subsequently licensed to Dr Reddy's Labs. A Phase 2 trial for use in patients with moderate-to-severe plaque psoriasis was completed in March 2020.

In some embodiments, the FAE in the methods of the present disclosure is VTS-72, a propriety combination of DMF and VTS-Aspirin, currently being developed by Vitalis for the treatment of patients with relapsing-remitting MS who experience dimethyl fumarate flush.

In some embodiments, for the methods described herein (e.g., for treating MS, a relapsing form of MS, including RRMS, SPMS and CIS, or other forms of MS, such as PPMS, RIS, etc.), the BTK inhibitor is BIIB-091 or a pharmaceutically acceptable salt thereof and the FAE is DMF. In some embodiments, for the methods described herein (e.g., for treating MS, relapsing form of MS, RRMS, SPMS, PPMS, CIS, RIS etc.), the BTK inhibitor is BIIB-091 or a pharmaceutically acceptable salt thereof and the FAE is DRF. In some embodiments, for the methods described herein (e.g., for treating MS, a relapsing form of MS, including RRMS, SPMS and CIS, or other forms of MS, such as PPMS, RIS, etc.), the BTK inhibitor is BIIB-091 or a pharmaceutically acceptable salt thereof and the FAE is MMF. In some embodiments, for the methods described herein (e.g., for treating MS, a relapsing form of MS, including RRMS, SPMS and CIS, or other forms of MS, such as PPMS, RIS, etc.), the BTK inhibitor is BIIB-091 or a pharmaceutically acceptable salt thereof and the FAE is XP-23839. In some embodiments, for the methods described herein (e.g., for treating MS, a relapsing form of MS, including RRMS, SPMS and CIS, or other forms of MS, such as PPMS, RIS, etc.), the BTK inhibitor is BIIB-091 or a pharmaceutically acceptable salt thereof and the FAE is VTS-72.

In some embodiments, for the methods described herein (e.g., for treating MS, a relapsing form of MS, including RRMS, SPMS and CIS, or other forms of MS, such as PPMS, RIS, etc.), the BTK inhibitor is fenebrutinib or a pharmaceutically acceptable salt thereof and the FAE is DMF. In some embodiments, for the methods described herein (e.g., for treating MS, a relapsing form of MS, including RRMS, SPMS and CIS, or other forms of MS, such as PPMS, RIS, etc.), the BTK inhibitor is fenebrutinib or a pharmaceutically acceptable salt thereof and the FAE is DRF. In some embodiments, for the methods described herein (e.g., for treating MS, a relapsing form of MS, including RRMS, SPMS and CIS, or other forms of MS, such as PPMS, RIS, etc.), the BTK inhibitor is fenebrutinib or a pharmaceutically acceptable salt thereof and the FAE is MMF. In some embodiments, for the methods described herein (e.g., for treating MS, a relapsing form of MS, including RRMS, SPMS and CIS, or other forms of MS, such as PPMS, RIS, etc.), the BTK inhibitor is fenebrutinib or a pharmaceutically acceptable salt thereof and the FAE is XP-23839. In some embodiments, for the methods described herein (e.g., for treating MS, a relapsing form of MS, including RRMS, SPMS and CIS, or other forms of MS, such as PPMS, RIS, etc.), the BTK inhibitor is fenebrutinib or a pharmaceutically acceptable salt thereof and the FAE is VTS-72.

In some embodiments, for the methods described herein (e.g., for treating MS, a relapsing form of MS, including RRMS, SPMS and CIS, or other forms of MS, such as PPMS, RIS, etc.), the BTK inhibitor is tolebrutinib or a pharmaceutically acceptable salt thereof and the FAE is DMF. In some embodiments, for the methods described herein (e.g., for treating MS, a relapsing form of MS, including RRMS, SPMS and CIS, or other forms of MS, such as PPMS, RIS, etc.), the BTK inhibitor is tolebrutinib or a pharmaceutically acceptable salt thereof and the FAE is DRF. In some embodiments, for the methods described herein (e.g., for treating MS, a relapsing form of MS, including RRMS, SPMS and CIS, or other form of MS, such as PPMS, RIS, etc.), the BTK inhibitor is tolebrutinib or a pharmaceutically acceptable salt thereof and the FAE is MMF. In some embodiments, for the methods described herein (e.g., for treating MS, a relapsing form of MS, including RRMS, SPMS and CIS, or other forms of MS, such as PPMS, RIS, etc.), the BTK inhibitor is tolebrutinib or a pharmaceutically acceptable salt thereof and the FAE is XP-23839. In some embodiments, for the methods described herein (e.g., for treating MS, a relapsing form of MS, including RRMS, SPMS and CIS, or other forms of MS, such as PPMS, RIS, etc.), the BTK inhibitor is tolebrutinib or a pharmaceutically acceptable salt thereof and the FAE is VTS-72.

In some embodiments, for the methods described herein (e.g., for treating MS, a relapsing form of MS, including RRMS, SPMS and CIS, or other forms of MS, such as PPMS, RIS, etc.), the BTK inhibitor is evobrutinib or a pharmaceutically acceptable salt thereof and the FAE is DMF. In some embodiments, for the methods described herein (e.g., for treating MS, a relapsing form of MS, including RRMS, SPMS and CIS, or other forms of MS, such as PPMS, RIS, etc.), the BTK inhibitor is evobrutinib or a pharmaceutically acceptable salt thereof and the FAE is DRF. In some embodiments, for the methods described herein (e.g., for treating MS, a relapsing form of MS, including RRMS, SPMS and CIS, or other forms of MS, such as PPMS, RIS, etc.), the BTK inhibitor is evobrutinib or a pharmaceutically acceptable salt thereof and the FAE is MMF. In some embodiments, for the methods described herein (e.g., for treating MS, a relapsing form of MS, including RRMS, SPMS and CIS, or other forms of MS, such as PPMS, RIS, etc.), the BTK inhibitor is evobrutinib or a pharmaceutically acceptable salt thereof and the FAE is XP-23839. In some embodiments, for the methods described herein (e.g., for treating MS, a relapsing form of MS, including RRMS, SPMS and CIS, or other forms of MS, such as PPMS, RIS, etc.), the BTK inhibitor is evobrutinib or a pharmaceutically acceptable salt thereof and the FAE is VTS-72.

In some embodiments, for the methods described herein (e.g., for treating MS, a relapsing form of MS, including RRMS, SPMS and CIS, or other forms of MS, such as PPMS, RIS, etc.), the BTK inhibitor is orelabrutinib, or a pharmaceutically acceptable salt thereof and the FAE is DMF. In some embodiments, for the methods described herein (e.g., for treating MS, a relapsing form of MS, including RRMS, SPMS and CIS, or other forms of MS, such as PPMS, RIS, etc.), the BTK inhibitor is orelabrutinib or a pharmaceutically acceptable salt thereof and the FAE is DRF. In some embodiments, for the methods described herein (e.g., for treating MS, a relapsing form of MS, including RRMS, SPMS and CIS, or other forms of MS, such as PPMS, RIS, etc.), the BTK inhibitor is orelabrutinib or a pharmaceutically acceptable salt thereof and the FAE is MMF. In some embodiments, for the methods described herein (e.g., for treating MS, a relapsing form of MS, including RRMS, SPMS and CIS, or other forms of MS, such as PPMS, RIS, etc.), the BTK inhibitor is orclabrutinib or a pharmaceutically acceptable salt thereof and the FAE is XP-23839. In some embodiments, for the methods described herein (e.g., for treating MS, a relapsing form of MS, including RRMS, SPMS and CIS, or other forms of MS, such as PPMS, RIS, etc.), the BTK inhibitor is orclabrutinib or a pharmaceutically acceptable salt thereof and the FAE is VTS-72.

Methods of Treatment

The present disclosure provides methods of treating a subject (e.g., a human patient) with an autoimmune disease, by administering to the subject a combination of a BTK inhibitor and a fumaric acid ester (FAE).

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Cocliac disease, dermatomyositis, diabetes mellitus type 1, Goodpasture's syndrome, Graves' disease, Guillain-Barre syndrome (GBS), Hashimoto's disease, idiopathic thrombocytopenia purpura, lupus, mixed connective tissue disease, systemic sclerosis (or systemic scleroderma), multiple sclerosis, psoriasis (e.g., plaque, guttate, inverse, pustular, or erythrodermic psoriasis), cytokine release syndrome, morphea, inflammatory bowel disease (IBD), dermatopolymyositis, myasthenia gravis, pemphigus vulgaris, pernicious anaemia, polymyositis, primary biliary cirrhosis, Sjögren's disease, temporal arteritis, Pemphigus (e.g., Pemphigus Vugaris (PV)), neuromyelitis optica (NMO), myasthenia gravis, autoimmune encephalitis (e.g., anti-NMDA receptor encephalitis), chronic inflammatory demyelinating polyneuropathy (CIDP), rheumatoid arthritis (RA), asthma, severe allergy and Wegener's granulomatosis.

In some embodiments, the autoimmune diseases can be treated with the present methods include multiple sclerosis (MS), lupus, rheumatoid arthritis (RA), Pemphigus Vugaris (PV) or Sjögren's disease. In some embodiments, the autoimmune diseases can be treated with the present methods include multiple sclerosis (MS), neuromyelitis optica (NMO), myasthenia gravis, lupus, chronic inflammatory demyelinating polyneuropathy (CIDP), anti-NMDA receptor encephalitis, and Sjögren's disease. In some embodiments, the autoimmune disease is multiple sclerosis. In other embodiments, the autoimmune disease is lupus.

In some embodiments, the present disclosure provides a method of treating a relapsing form of MS. The method comprises administering to the subject a combination of a BTK inhibitor and a fumaric acid ester (FAE). As used herein, a "relapsing form of MS" includes clinically isolated syndrome (CIS), relapsing-remitting disease (RRMS), and active secondary progressive disease. In some embodiments, the methods can be used for treating MS selected from relapsing-remitting MS (RRMS), secondary progressive MS (SPMS), non-relapsing SPMS, primary progressive MS (PPMS), clinically isolated syndrome (CIS), and radiologically isolated syndrome (RIS).

CIS is a first episode of neurologic symptoms caused by inflammation and demyelination in the central nervous system. The episode, which by definition must last for at least 24 hours, is characteristic of multiple sclerosis but does not yet meet the criteria for a diagnosis of MS because people who experience a CIS may or may not go on to develop MS. When CIS is accompanied by lesions on a brain MRI (magnetic resonance imaging) that are similar to those seen in MS, the person has a high likelihood of a second episode of neurologic symptoms and diagnosis of relapsing-remitting MS. When CIS is not accompanied by MS-like lesions on a brain MRI, the person has a much lower likelihood of developing MS.

RRMS, the most common disease course of MS, is characterized by clearly defined attacks of new or increasing neurologic symptoms. These attacks—also called relapses or exacerbations—are followed by periods of partial or complete recovery (remissions). During remissions, all symptoms may disappear, or some symptoms may continue and become permanent. However, there is no apparent progression of the disease during the periods of remission. RRMS can be further characterized as either active (with relapses and/or evidence of new MRI activity over a specified period of time) or not active, as well as worsening (a confirmed increase in disability following a relapse) or not worsening.

SPMS follows an initial relapsing-remitting course. Some people who are diagnosed with RRMS will eventually transition to a secondary progressive course in which there is a progressive worsening of neurologic function (accumulation of disability) over time. SPMS can be further characterized as either active (with relapses and/or evidence of new MRI activity during a specified period of time) or not active, as well as with progression (evidence of disability accumulation over time, with or without relapses or new MRI activity) or without progression.

PPMS is characterized by worsening neurologic function (accumulation of disability) from the onset of symptoms, without early relapses or remissions. PPMS can be further characterized as either active (with an occasional relapse and/or evidence of new MRI activity over a specified period of time) or not active, as well as with progression (evidence of disability accumulation over time, with or without relapse or new MRI activity) or without progression.

Patients diagnosed with RIS do not present any overt symptoms of MS, but exhibit brain abnormality (e.g., observed by magnetic resonance imaging (MRI)) that are similar to what is seen in patients with MS. Diagnosis of RIS often occurs during a brain scan due to unrelated conditions, such as headache, migraines, head injury, stroke etc. Although there is a strong association between RIS and MS (RIS often indicates the earliest detectable preclinical phase of the disease), patients with RIS may not go on to develop MS.

In certain embodiments, the present disclosure provides a method of treating a subject with lupus. In certain embodiments, the present disclosure provides a method of treating a relapsing form of lupus. In some embodiments, lupus is systemic lupus erythematosus (SLE). In other embodiments, lupus is cutaneous lupus erythematosus (CLE). In some embodiments, lupus is discoid lupus erythematosus. In some embodiments, the present disclosure provides a method of treating lupus nephritis. In some embodiments, the present disclosure provides a method of treating a subject with moderate SLE. In certain embodiments, the subject has moderate SLE without severe active CNS and/or severe active renal involvement. In certain embodiments, the subject has moderate SLE with severe active CNS and/or severe active renal involvement. In certain embodiments, the subject has cutaneous manifestations of SLE (e.g., malar or discoid rash). In certain embodiments, the subject has severe SLE. In certain embodiments, the subject has severe SLE without severe active CNS and/or severe active renal involvement. In certain embodiments, the subject has severe SLE with severe active CNS and/or severe active renal involvement. Moderate or severe lupus is a staging of lupus (see, e.g., Guidelines for Referral and Management of Systemic Lupus Erythematosus in Adults, Arthritis & Rheumatism, 42(9): 1785-1795 (1999); Gladman, Prognosis and treatment of systemic lupus erythematosus, Curr. Opin. Rheumatol., 8:430-437 (1996); Kalunian et al, Definition, classification, activity and damage indices. In: Dubois' lupus erythematosus. $5^{th}$ ed., Baltimore: Williams and Wilkins; pp. 19-30 (1997)).

SLE is the most common type of lupus. People with SLE may experience a variety of symptoms that include fatigue, skin rashes, fevers, and pain or swelling in the joints. Among some adults, having a period of SLE symptoms—called flares—may happen every so often, sometimes even years apart, and go away at other times—called remission. However, other adults may experience SLE flares more frequently throughout their life. Other symptoms can include sun sensitivity, oral ulcers, arthritis, lung problems, heart problems, kidney problems, seizures, psychosis, and blood cell and immunological abnormalities.

CLE is lupus affecting the skin, in which the body's immune system attacks healthy skin. There are 3 main types: (1) Acute cutaneous lupus ("acute skin lupus"); (2) Subacute cutaneous lupus ("subacute lupus"); and (3) Chronic cutaneous lupus ("discoid lupus"). Each type of skin lupus can be triggered and worsened by sunlight. Acute skin lupus most often involves a prominent rash on the checks and nose ("butterfly rash"). Subacute lupus most often presents with a red, raised, scaly rash on sun-exposed areas of the body. It tends to have circular skin lesions or lesions that can look like psoriasis on sun-exposed skin. Discoid lupus starts out as a red to purple scaly rash on the scalp, face, cars, and other sun-exposed areas. Over time, discoid lupus may heal with discolored scarring and even hair loss when the scalp is involved. Sometimes patients may feel pain or itch.

In the disclosed methods, the BTK inhibitor and the FAE are administered in combination or used as a combination therapy. A combination therapy is meant to encompass administration of the two or more therapeutic agents to a single subject, and are intended to include treatment regimens in which the agents are administered by the same or different route of administration or at the same or different times. They include simultaneous administration in separate compositions, simultaneous administration in the same composition and administration at different times in separate compositions. For the present disclosure, the BTK inhibitor and the FAE can be administered by the same or different route of administration or at the same or different times. In some embodiments, the BTK inhibitor and the FAE are administered at the same time. In some embodiments, the BTK inhibitor and the FAE are administered sequentially. In certain embodiments, the BTK inhibitor is administered before the FAE. In certain embodiments, the BTK inhibitor is administered after the FAE.

As used herein, the terms "subject" and "patient" may be used interchangeably, and mean a mammal in need of treatment, e.g., a human, companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

An "effective amount" of the BTK inhibitor is an amount sufficient to provide a therapeutic benefit in the treatment of disease or disorder described herein or to delay or minimize one or more symptoms associated with the disorder or disease when combined with a FAE. An "effective amount" of the FAE as described herein, is an amount sufficient to provide a therapeutic benefit in the treatment of a disorder or disease described herein or to delay or minimize one or more symptoms associated with the disorder or disease when combined with the BTK inhibitor. The term "therapeutically effective amount" and "effective amount" are used interchangeably. The term "effective amount" can encompass an amount that improves overall therapy, reduces or avoids symptoms, signs, or causes of the condition, and/or enhances the therapeutic efficacy of another therapeutic agent. In certain embodiments, an effective amount is an amount sufficient for eliciting therapeutic effects in the treatment of an autoimmune disease descried herein (e.g., MS, lupus etc.). In some embodiments, an effective amount for the BTK inhibitor that can be used in the combination treatment methods described herein is the same amount when BTK inhibitor is used as a single agent. In some embodiments, an effective amount for the FAE that can be used in the combination treatment methods described herein is the same amount when FAE is used as a single agent. In some embodiments, an effective amount for the BTK inhibitor that can be used in the combination treatment methods described herein is less than the amount when BTK inhibitor is used as a single agent. In some embodiments, an effective amount for the FAE that can be used in the combination treatment methods described herein is less than the amount when FAE is used as a single agent.

In some embodiments, for the methods of the present disclosure, the effective amount of the BTK inhibitors and/or the FAEs described herein, or a pharmaceutically acceptable salt thereof, can be 10 μg-2000 mg or 10 μg-500 mg.

In some embodiments, a standard dose of the BTK inhibitor or the FAE can be used in the combination therapy of the present disclosure. As used herein, a "standard dose" refers to the total daily dosage amount for the compounds used in monotherapies, i.e., the compound is used as a single agent.

For example, in some embodiments, when the FAE is DMF, the total daily dose of DMF can be administered in the present combination therapy is 480 mg (e.g., 240 mg administered twice daily), the same dose currently used as the single agent (i.e., monotherapy) for treating MS. In some embodiments, when the FAE is DMF, a starting total daily dose of 240 mg (e.g., 120 mg administered twice daily) can be administered for 7 days, followed by a total daily dose of 480 mg (e.g., 240 mg administered twice daily) as the maintenance dose. In some embodiments, a total daily dose of 924 mg (e.g., 462 mg administered twice daily) of DRF can be used in the present combination therapy, the same dose used as monotherapy. In some embodiments, a total daily dose of 462 mg (e.g., 231 mg administered twice daily) of DRF can be administered as the starting dose for 7 days, followed by a total daily dose of 924 mg (e.g., 462 mg administered twice daily) as the maintenance dose. In some embodiments, when the FAE is MMF (e.g., Bafiertam™), a total daily dose of 190 mg (e.g., 95 mg administered twice daily) can be administered as the starting dose for 7 days, followed by a total daily dose of 380 mg (e.g., 190 mg administered twice daily) as the maintenance dose. The total daily doses described above can be administered twice a day or once a day.

In some embodiments, when the BTK inhibitor is fenebrutinib, the standard dose is 200 mg twice a day. In some embodiments, when the BTK inhibitor is fenebrutinib, the standard dose is 150 mg once a day. In some embodiments, when the BTK inhibitor is evobrutinib, the standard dose is 50 mg twice a day, or 75 mg twice a day or 75 mg once a day. In some embodiments, when the BTK inhibitor is tolebrutinib, the standard dose is 60 mg once a day.

In certain embodiments, for the combination therapies described in the present disclosure, a low dose of the BTK inhibitor or a low dose of the FAE can be used. As used herein, a "low dose" means a dose that is 50-90%, 60-80%, 70-80%, 74-76% or 75% of the standard dose. In some embodiments, when the FAE is DMF, a total daily dose in the range of 240 mg to 432 mg, 288 mg to 384 mg, 336 mg to 384 mg, or 355 mg to 365 mg can be used in the present combination therapies. In some embodiments, when the FAE is DMF, a total daily dose in the range of 120 mg to 216 mg, 144 mg to 192 mg, 168 mg to 192 mg, or 177.5 mg to 182.5 mg can be used as the starting dose for 7 days, followed by a total daily dose in the range of 240 mg to 432 mg, 288 mg to 384 mg, 336 mg to 384 mg, or 355 mg to 365 mg as the maintenance dose. In some embodiments, a total daily dose of 360 mg (e.g., 180 mg administered twice daily) of DMF can be used in the present methods. In some embodiments, a total daily dose of 180 mg (e.g., 90 mg administered twice daily) of DMF can be administered as the starting dose for 7 days, followed by a total daily dose of 360 mg (e.g., 180 mg administered twice daily) as the maintenance dose. In some embodiments, when the FAE is DRF, a total daily dose in the range of 462 mg to 832 mg, 553 mg to 739 mg, or 647 mg to 739 mg can be used in the present combination therapies. In some embodiments, when the FAE is DRF, a total daily dose in the range of 231 mg to 416 mg, 276.5 mg to 369.5 mg, or 323.5 mg to 369.5 mg as the starting dose for 7 days, followed by a total daily dose in the range of 462 mg to 832 mg, 553 mg to 739 mg, or 647 mg to 739 mg as the maintenance dose. In some embodiments, a total daily dose of 693 mg (e.g., 346.5 mg administered twice daily) of DRF can be used in the present methods. In some embodiments, a total daily dose of 346.5 mg (e.g., 173.25 mg administered twice daily) of DRF can be administered as the starting dose for 7 days, followed by a total daily dose of 693 mg (e.g., 346.5 mg administered twice daily) as the maintenance dose. In some embodiments, when the FAE is MMF (e.g., Bafiertam™), a total daily dose in the range of 190 mg to 361 mg, 228 mg to 304 mg or 266 mg to 304 mg can be used in the present combination therapy. In some embodiments, when the FAE is MMF (e.g., Bafiertam™), a total daily dose in the range of 95 mg to 180.5 mg, 114 mg to 152 mg, or 133 mg to 152 mg can be used as the starting dose for 7 days, followed by a total daily dose in the range of 190 mg to 361 mg, 228 mg to 304 mg or 266 mg to 304 mg as the maintenance dose. In some embodiments, a total daily dose of 285 mg of MMF (e.g., Bafiertam™) can be used in the present methods. In some embodiments, a total daily of 142.5 mg of MMF (e.g., Bafiertam™) is administered as the starting dose for 7 days, followed by a total daily dose of 285 mg as the maintenance dose. The total daily doses described above can be administered twice a day or once a day.

The BTK inhibitor and the FAE described herein, or a pharmaceutically acceptable salt thereof, can be administered by any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician.

The a compound or pharmaceutically acceptable salt thereof as described herein can be conveniently administered in unit dosage form.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

The present disclosure also provides pharmaceutical compositions that include a BTK inhibitor, a FAE, and typically at least one additional substance, such as a pharmaceutically acceptable carrier or diluent. In some embodiments, the pharmaceutical composition comprises BIIB-091 or a pharmaceutically acceptable salt thereof, DMF, and at least one pharmaceutically acceptable carrier or diluent. In some embodiments, the pharmaceutical composition comprises BIIB-091 or a pharmaceutically acceptable salt thereof, DRF, and at least one pharmaceutically acceptable carrier or diluent. In some embodiments, the pharmaceutical composition comprises BIIB-091 or a pharmaceutically acceptable salt thereof, MMF, and at least one pharmaceutically acceptable carrier or diluent. In some embodiments, the pharmaceutical composition comprises BIIB-091 or a pharmaceutically acceptable salt thereof, XP-23839, and at least one pharmaceutically acceptable carrier or diluent. In some embodiments, the pharmaceutical composition comprises BIIB-091 or a pharmaceutically acceptable salt thereof, VTS-72, and at least one pharmaceutically acceptable carrier or diluent.

In some embodiments, the pharmaceutical composition comprises fenebrutinib or a pharmaceutically acceptable salt thereof, DMF, and at least one pharmaceutically acceptable carrier or diluent. In some embodiments, the pharmaceutical composition comprises fenebrutinib or a pharmaceutically acceptable salt thereof, DRF, and at least one pharmaceutically acceptable carrier or diluent. In some embodiments, the pharmaceutical composition comprises fenebrutinib or a pharmaceutically acceptable salt thereof, MMF, and at least one pharmaceutically acceptable carrier or diluent. In some embodiments, the pharmaceutical composition comprises fenebrutinib or a pharmaceutically acceptable salt thereof, XP-23839, and at least one pharmaceutically acceptable carrier or diluent. In some embodiments, the pharmaceutical composition comprises fenebrutinib or a pharmaceutically acceptable salt thereof, VTS-72, and at least one pharmaceutically acceptable carrier or diluent.

In some embodiments, the pharmaceutical composition comprises tolebrutinib or a pharmaceutically acceptable salt thereof, DMF, and at least one pharmaceutically acceptable carrier or diluent. In some embodiments, the pharmaceutical composition comprises tolebrutinib or a pharmaceutically acceptable salt thereof, DRF, and at least one pharmaceutically acceptable carrier or diluent. In some embodiments, the pharmaceutical composition comprises tolebrutinib or a pharmaceutically acceptable salt thereof, MMF, and at least one pharmaceutically acceptable carrier or diluent. In some embodiments, the pharmaceutical composition comprises tolebrutinib or a pharmaceutically acceptable salt thereof, XP-23839, and at least one pharmaceutically acceptable carrier or diluent. In some embodiments, the pharmaceutical composition comprises tolebrutinib or a pharmaceutically acceptable salt thereof, VTS-72, and at least one pharmaceutically acceptable carrier or diluent.

In some embodiments, the pharmaceutical composition comprises evobrutinib or a pharmaceutically acceptable salt thereof, DMF, and at least one pharmaceutically acceptable carrier or diluent. In some embodiments, the pharmaceutical composition comprises evobrutinib or a pharmaceutically acceptable salt thereof, DRF, and at least one pharmaceutically acceptable carrier or diluent. In some embodiments, the pharmaceutical composition comprises evobrutinib or a pharmaceutically acceptable salt thereof, MMF, and at least one pharmaceutically acceptable carrier or diluent. In some embodiments, the pharmaceutical composition comprises evobrutinib or a pharmaceutically acceptable salt thereof, XP-23839, and at least one pharmaceutically acceptable carrier or diluent. In some embodiments, the pharmaceutical composition comprises evobrutinib or a pharmaceutically acceptable salt thereof, VTS-72, and at least one pharmaceutically acceptable carrier or diluent.

In some embodiments, the pharmaceutical composition comprises orelabrutinib or a pharmaceutically acceptable salt thereof, DMF, and at least one pharmaceutically acceptable carrier or diluent. In some embodiments, the pharmaceutical composition comprises orclabrutinib or a pharmaceutically acceptable salt thereof, DRF, and at least one pharmaceutically acceptable carrier or diluent. In some embodiments, the pharmaceutical composition comprises orelabrutinib or a pharmaceutically acceptable salt thereof, MMF, and at least one pharmaceutically acceptable carrier or diluent. In some embodiments, the pharmaceutical composition comprises orelabrutinib or a pharmaceutically acceptable salt thereof, XP-23839, and at least one pharmaceutically acceptable carrier or diluent. In some embodiments, the pharmaceutical composition comprises orelabrutinib or a pharmaceutically acceptable salt thereof, VTS-72, and at least one pharmaceutically acceptable carrier or diluent.

The pharmaceutical composition of the invention is formulated to be compatible with its intended route of administration. In an embodiment, the composition is formulated in accordance with routine procedures as a pharmaceutical composition adapted for intravenous, subcutancous, intramuscular, oral, intranasal, or topical administration to human beings.

EXEMPLIFICATIONS

Example 1. In Vivo Study in Murine Model of Multiple Sclerosis

The goal of the study is to compare efficacy of diroximel fumarate (Vumerity) alone, BIIB091 alone, and the combination diroximel fumarate and BIIB091 in B cell-dependent experimental autoimmune encephalomyelitis (EAE). B cells are required for experimental autoimmune encephalomyelitis (EAE) induced by immunization of female C57BL/6J mice with full length recombinant human myelin oligodendrocyte glycoprotein (MOG) $hMOG_{1-125}$ in adjuvant (Oliver, A. R. et al. "Rat and human myelin oligodendrocyte glycoproteins induce experimental autoimmune encephalomyelitis by different mechanisms in C57BL/6 mice." *J Immunol* (2003). 171(1): 462-468; Lyons, J. et al "B cells are critical to induction of experimental allergic encephalomyelitis by protein but not by a short encephalitogenic peptide". *Eur. J. Immunol.* (1999), 29: 3432-3439).

1. Key Study Parameters

TABLE 1

| | |
|---|---|
| **MODEL** | |
| Description | Prophylactic EAE |
| Animal strain(s) & gender(s) | C57BL/6 mice, females |
| Day 0 | Day of immunization |
| Study length | 30 Days (Day −1 to Day 28) |
| **ANIMALS & GROUPS** | |
| Total number of animals | 80 |
| Source of animals | Taconic Biosciences (breeder) |
| Age at start of study (Day 0) | 9 to 13 weeks |
| Number of groups | 4 |
| Group size | 20 animals (per Table 2) |
| Group assignment day(s) | Day −1 |
| **TREATMENT** | |
| First dosing | Day 0 |
| Last dosing | Day 27 |
| **READOUTS** | |
| First scoring | Day 7 after immunization |
| Last scoring | End of study, Day 28 |
| Scoring frequency | Daily |
| First weighing | Day −1 |
| Last weighing | End of study |
| Weighing frequency | 3×/week (Monday, Wednesday, Friday) |
| Tissue collection & analysis | Serum; other optional, can be ordered with 5 days' notice |

2. Animals

Female mice at 9-13 weeks of age (age-matched within one week) were ordered from Taconic Biosciences and given standard water and chow ad libitum throughout the duration of the experiment. Mice were acclimated to the vivaria for at least 7 days prior to the start of the study.

3. EAE Induction

EAE was induced in all mice as follows:

| | |
|---|---|
| Day 0, Hour 0: | Immunization with $MOG_{1-125}$/CFA |
| Day 0, Hour 2: | Injection of pertussis toxin |
| Day 1, Hour 0: | $2^{nd}$ injection of pertussis toxin (24 hours after initial immunization) |

Mice were injected subcutaneously at 2 sites in the back with the emulsion component (containing $MOG_{1-125}$) of Hooke Kit™ $MOG_{1-125}$/CFA Emulsion PTX, catalog number EK-2160 (Hooke Laboratories, Lawrence MA). The first site of injection was in the upper back, approximately 1 cm caudal of the neck line. The second site was in the lower back, approximately 2 cm cranial of the base of the tail. The injection volume was 0.1 mL at each site.

Within 2 hours of the injection of emulsion, and then again 24 hours after the injection of emulsion, the pertussis toxin component of the kit was administered intraperitoneally.

4. Groups and Dosing

Mice were assigned to groups in a balanced manner to achieve similar average weight across the groups at the start of the study (Day −1). Table 2 below describes the treatment administered to each group. Dosing volume of all treatments was 5 mL/kg. Both treatment compounds were formulated in the same vehicle: (0.5% HPMC E50 premium LV/0.2% Tween 20 pH 4 (50 mM Citrate Buffer)

TABLE 2

Treatment regimen

| Group | # animals | Treatment 1 | Dose | Route and frequency | Treatment 2 | Dose | Route and frequency | Purpose |
|---|---|---|---|---|---|---|---|---|
| 1 | 20 | Vehicle | — | p.o., BID | Vehicle | — | p.o., BID | Negative control |
| 2 | 20 | BIIB091 | 50 mpk | p.o., BID | Vehicle | — | p.o., BID | monotherapy |
| 3 | 20 | Vehicle | — | p.o., BID | DRF | 90 mpk | p.o., BID | monotherapy |
| 4 | 20 | BIIB091 | 50 mpk | p.o., BID | DRF | 90 mpk | p.o., BID | combo therapy |

Dosing of all mice started on Day 0 and continued through Day 27. Dosing for each treatment was at the same time (+/−1 hour) each dosing day. There were at least 30 and not more than 90 minutes between administration of Treatments 1 and 2. There were no less than 10 and no more than 14 hours between doses of the same article 5. Readouts and Statistics a. Scoring and Readouts Readouts are EAE scores and body weight. Body weight were measured 3 times/week (Monday, Wednesday, Friday; weighing may be delayed 1 day if these fall on a major US holiday), starting on Day −1. Animals were scored daily starting from Day 7. All readouts continued until termination of the study.

Scoring was performed blind, by a person unaware both of treatment and of previous scores for each mouse.

EAE Scoring

EAE was scored on the scale of 0 to 5 according to scoring criteria in Table 3 below:

TABLE 3

EAE scoring criteria

| Score | Clinical observations |
|---|---|
| 0 | No obvious changes in motor functions of the mouse in comparison to non-immunized mice.<br>When picked up by the tail, the tail has tension and is erect. Hind legs are usually spread apart. When the mouse is walking, there is no gait or head tilting. |
| 1 | Limp tail.<br>When the mouse is picked up by its tail, the whole tail drapes over your finger, instead of being erect. |
| 2 | Limp tail and weakness of hind legs.<br>When mouse is picked up by its tail, legs are not spread apart but held closer together. When the mouse is observed when walking, it has an obviously wobbly walk. |
| 3 | Limp tail and complete paralysis of hind legs (most common).<br>OR<br>Limp tail with paralysis of one front and one hind leg.<br>OR<br>ALL of:<br>Severe head tilting,<br>Walking only along the edges of the cage,<br>Pushing against the cage wall,<br>Spinning when picked up by the tail. |
| 4 | Limp tail, complete hind leg and partial front leg paralysis.<br>Mouse is minimally moving around the cage but appears alert and feeding. Usually, euthanasia is recommended after the mouse scores 4 for 2 days. When the mouse is euthanized due to severe paralysis, a score of 5 is entered for that mouse for the remainder of the experiment. |
| 5 | Complete hind and complete front leg paralysis, no movement around the cage.<br>OR<br>Mouse is spontaneously rolling in the cage.<br>OR<br>Mouse is found dead due to paralysis. |

In-between scores were assigned when the clinical signs fall between two above defined scores.

b. Statistical Analysis

Hooke's standard statistical analysis for EAE studies was applied, according to Table 4 below.

TABLE 4

Statistical analysis performed

| Readout | Statistical analysis |
|---|---|
| EAE incidence | Chi-square test |
| Mean day of EAE onset (sick animals) | 2-tailed Student's t-test |
| Median day of EAE onset (all animals) | Wilcoxon's survival test |
| Average clinical score | Plotted only |
| Average end clinical score | Wilcoxon's non-parametric test |
| Mean maximum score (MMS) | Wilcoxon's non-parametric test |
| Average weight gain/loss | 2-tailed Student's t-test, plotted |
| End weight gain/loss | 2-tailed Student's t-test |

c. Serum Collection

On Day −1, three (3) mice from each group were bled and serum isolated (baseline serum). On Days 14, 21, and 28, all mice were bled and serum isolated. Serum was shipped to on dry ice at the end of the study for analyses.

Figure 2:
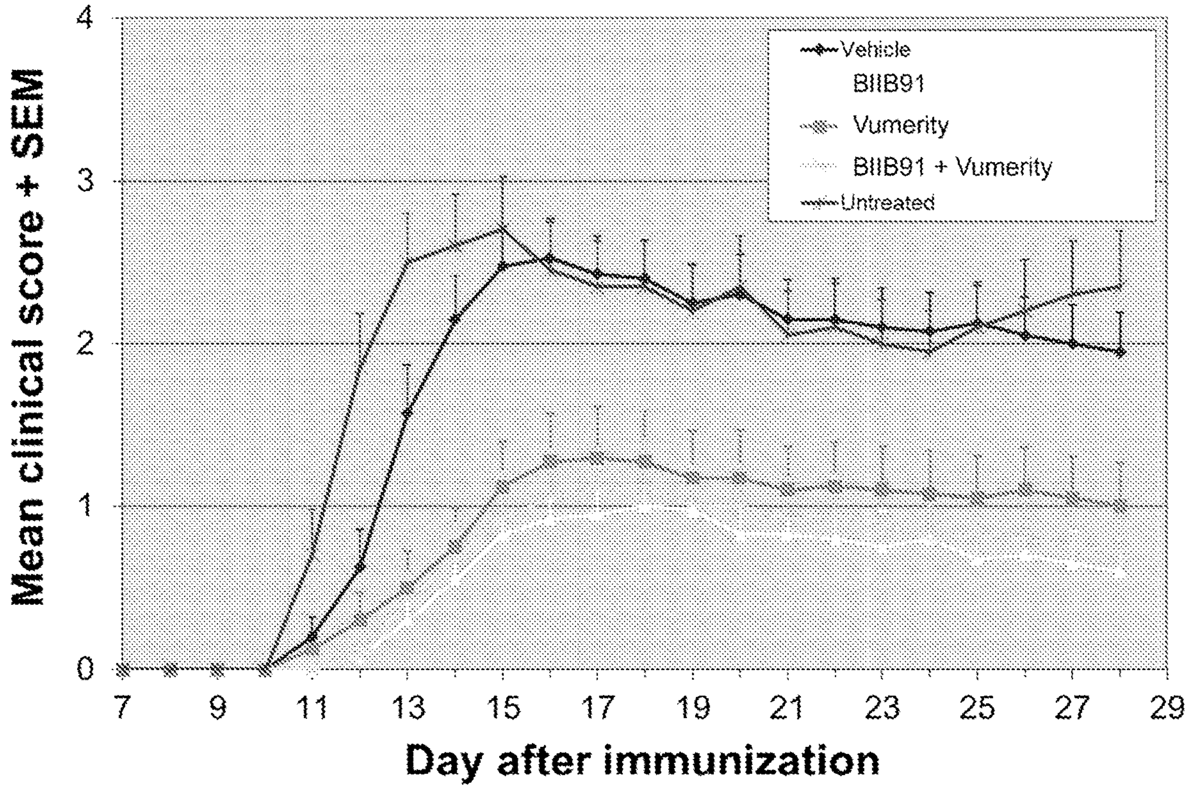
FIG. 2 shows EAE severity (mean clinical score vs. time) for each treatment group in the in vivo murine model of multiple sclerosis.
Figure 3:
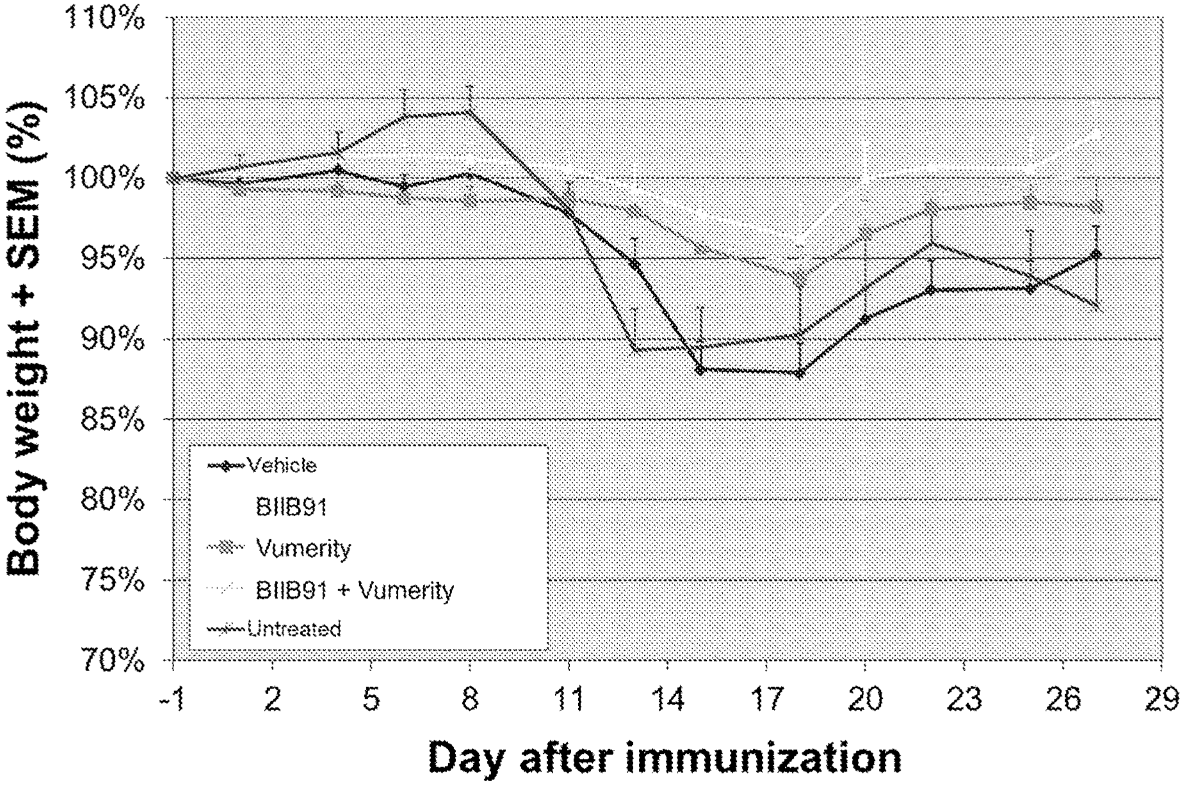
FIG. 3. shows body weight over time for each treatment group in the in vivo murine model of multiple sclerosis.

As summarized in Table 5 below and FIGS. 1-3, the in vivo study in murine model of multiple sclerosis indicates that the BIIB091+DRF combination group was efficacious at postponing disease onset and reducing disease incidence and severity in this study. Mean maximum score, end score, and end body weight data demonstrate that all compound treatment groups had lower disease incidence and less severe EAE compared to vehicle treatment (FIG. 1). EAE severity (mean clinical score vs. time) was ameliorated and disease onset significantly delayed in all treatment groups compared to vehicle (FIG. 2). Clinical improvement is usually accompanied by increased body weight. At the end of the study a weight gain significantly higher than the negative control group is indicative of drug efficacy (FIG. 3).

TABLE 5

Summary of results from in vivo study in murine model of multiple sclerosis

| Treatment | EAE incidence | Median day of onset (all mice) | MMS +/− SD | End score +/− SD | End % body weight +/− SD |
|---|---|---|---|---|---|
| Vehicle | 90.0% | 13.0 | 2.63 +/− 1.10 | 1.95 +/− 1.09 | 95.3% +/− 7.6% |
| BIIB091 | 45.0%[a] | >28.0[a]* | 1.13 +/− 1.38[a] | 0.60 +/− 0.88[a] | 102.8% +/− 8.3%[a] |
| DRF | 50.0%[a] | >28.0[a]* | 1.45 +/− 1.52[a] | 1.00 +/− 1.19[a] | 98.2% +/− 8.3% |
| BIIB091 + DRF | 50.0%[a] | >28.0[a]* | 1.23 +/− 1.38[a] | 0.73 +/− 0.94[a] | 100.4% +/− 5.8%[a] |
| Untreated | 90.0% | 11.0[a] | 2.75 +/− 1.06 | 2.35 +/− 1.08 | 92.0% +/− 13.0% |

[a]$p < 0.05$ vs. vehicle

*Median day of onset cannot be calculated if ≤50% of mice developed disease

Lymphadenopathy Scoring Criteria:

Palpate each pair of nodes or node clusters in each of the three sites (defined above) and the scoring is based on the following:

0=no palpable nodes (defined as >~3 mm) at any of the three sites 1 to 6=Estimate the diameter of each palpable node or cluster on each side of the body in each of the three sites, (e.g, left and right inguinal); add the diameters together and score as a 1 if the total is less than 1 cm, and a 2 if more than 1 cm; then add the totals for each of the three sites, for a maximum score of 2/area×3 areas=6.

Skin Lesion Scoring Criteria:

Determine which cages of mice exhibit "barbering" (defined as cages in which all mice in the cage except one show hair and whiskers neatly removed from—usually—the cheek areas). Only score barbered mouse areas positive if additional disruption of skin integrity or scabbing occurs later (generally after week 12). Most lesions occur on upper back or head.

0=none

1=1 or 2 small lesions 2-4 mm in length at any site

2=lesion(s) more extensive than 1 above, but with avg. diameter<0.5 cm

3=lesion(s) with average diameter≥0.5, but ≤1.0 cm

4=lesion(s) with average diameter>1 cm

Proteinuria Scoring Criteria (0-5):

Hold mouse upside down and express 1 or 2 drops of urine by applying pressure to the abdomen. Capture urine on an Albustix test strip and determine score by matching to color code on bottle between 1 and 2 minutes later.

0=none

1=1 to 30 mg/dL

2=31 to 99 mg/dL

3=100 to 299 mg/dL

4=300 to 1999 mg/dL

5=>2000 mg/dL

Serum Cytokine and Chemokine Level Determination

The following serum cytokines and chemokines were assessed using Luminex assays: IL-1B, IL-2, IL-4, IL-5, IL-6, IL-10, IL-12, IL-13, IL-15, IL-17A, IL-17E, IL-17F, IL-21, IL-22, IL-23, IL-27, IL-28B, IL-31 and IL-33; sCD40L, GM-CSF, IFNγ, MIP-3α, TNFα and TNFβ.

Flow Cytometry:

Flow cytometry is used to determine the following biomarkers, which are used to measure activated B cells (CD19+CD69+CD62L−), activated T cells (CD3+CD4+CD69+, CD3+CD8+CD69+) (CD3+CD4+CD62L−,

Example 2. In Vivo Study of Mice Model of Lupus

MRL/MpJ-Fas$^{lpr}$/J (MRL-lpr) (hereinafter MRL/LPR mice) mice develop an autoimmune disease resembling systemic lupus erythematosus (SLE). These mice have a severe disease progression involving anti-DNA antibodies, fatal glomerulonephritis, vasculitis, skin lesions, lymphadenopathy and splenomegaly. The causative mutation in this strain of mice is a loss of function in the death receptor Fas and disease onset is accelerated in female mice as compared to males. For this reason, female mice were chosen for these experiments.

Female MRL/LPR mice were ordered from the Jackson laboratory and all experiments were conducted a Boulder Biopath.

Female mice were dosed orally beginning at 9 weeks of age with BIIB091 alone, DRF alone, BIIB091 and DRF in combination or the vehicle control twice daily (BID) for 11 weeks. BIIB091 was dosed at 50 mg/kg, while DRF was dosed at 90 mg/kg, respectively. Cyclophosphamide (CPA) was used as a positive control in the study and was administered through intraperitoneal injection (IP) once daily at 15 mg/kg.

Efficacy of test articles was based on urine proteinuria levels, lymphadenopathy scores, skin lesion scores, tissue weights (kidney, spleen, and lymph nodes), skin and kidney histopathology, serum anti-DNA antibody levels, cytokine and chemokine levels. Additionally, flow cytometry was performed to evaluate the test article impact on activated B cells and T cells as well as plasma blasts.

CD44+) (CD3+CD8+CD62L−, CD44+) and plasmablasts (CD19+/−, CD138+, CD44++) in the spleen.

| Flow Cytometry Reagents | Biomarkers |
| --- | --- |
| FITC | CD19 |
| BV786 | CD45 |
| PE | CD62L |
| BB700 | CD4 |
| PE-Cy7 | CD8 |
| BV605 | CD44 |
| BV421 | CD138 |
| Alexa 700 | CD69 |
| BV510 | CD3 |

Treatment with DRF did not show efficacy in this mice model. Treatment with the BIIB091+DRF combination was efficacious, similar to that observed for BIIB091.

Example 3. In Vitro CD69 Inhibition in MS Patients' Blood Samples

Healthy control and multiple sclerosis (MS) patient whole blood were sourced from Sanguine Biosciences, including three patient cohorts: 3 healthy controls, 3 MS patients treated with DMF for more than 3 months, and 3 MS patients not on treatment or treated with non-DMF disease modifying therapies (DMTs). Samples were received one day after blood collection and incubated with DMSO (control) or titrating concentrations of BIIB-091 at 37° C. for 30 minutes prior to B cell (CD69) or basophil (C63)activation. Assessment of B cell-receptor-mediated CD69 upregulation and Fc epsilon receptor-driven CD63 expression on basophils were performed according to the following assay protocols.

CD69 Assay

Upon pre-incubation with BIIB-091 or DMSO, whole blood sample was stimulated overnight with dextran conjugated anti-human IgD or PBS as control. Following treatment, whole blood was subjected to antibody staining with fluorochrome-labeled lineage antibodies containing anti-human CD69-APC (clone L78, BD Biosciences) and anti-human CD19-PE (clone HIB 19, BD Biosciences). After red blood cell lysis and leukocytes fixation, the extent of CD69 expression on $CD19^+$ B cells was analyzed by flow cytometry. A non-linear regression curve fit (variable slope) was used to determine the BIIB-091 $IC_{50}$ value.

Basophil Assay

Upon pre-incubation with BIIB-091 or DMSO, whole blood sample was then subjected to pre-stimulation with recombinant human IL-3 (R&D Systems) for 10 minutes, followed by 20-minute stimulation with polyclonal anti-human IgE (Bethyl Laboratories) or PBS as control. Staining with fluorochrome-labeled lineage antibodies was carried out for treated whole blood. After red blood cell lysis and leukocytes fixation, the frequency of basophils expressing CD63 was analyzed by flow cytometry. A non-linear regression curve fit (variable slope) was used to determine the BIIB-091 $IC_{50}$ value.

Results

Figure 4:
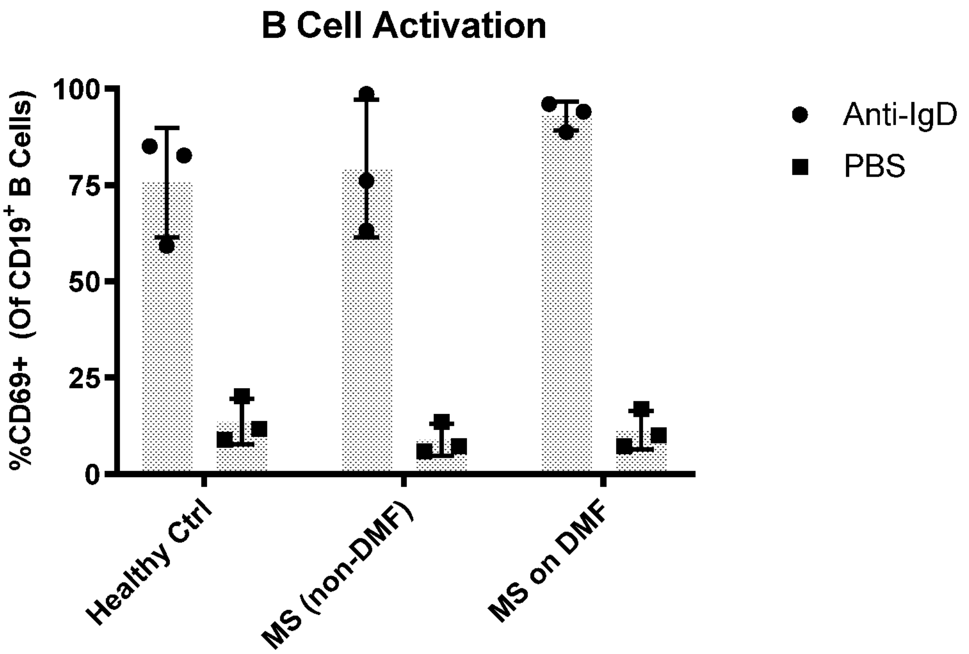
FIG. 4 shows C69 upregulation on $CD19^+$ cells with anti-IgD stimulation across all three patient cohort tested: healthy controls, MS patients treated with DMF, and MS patients not on treatment or treated with non-DMF disease modifying therapies (DMTs).
Figure 5:
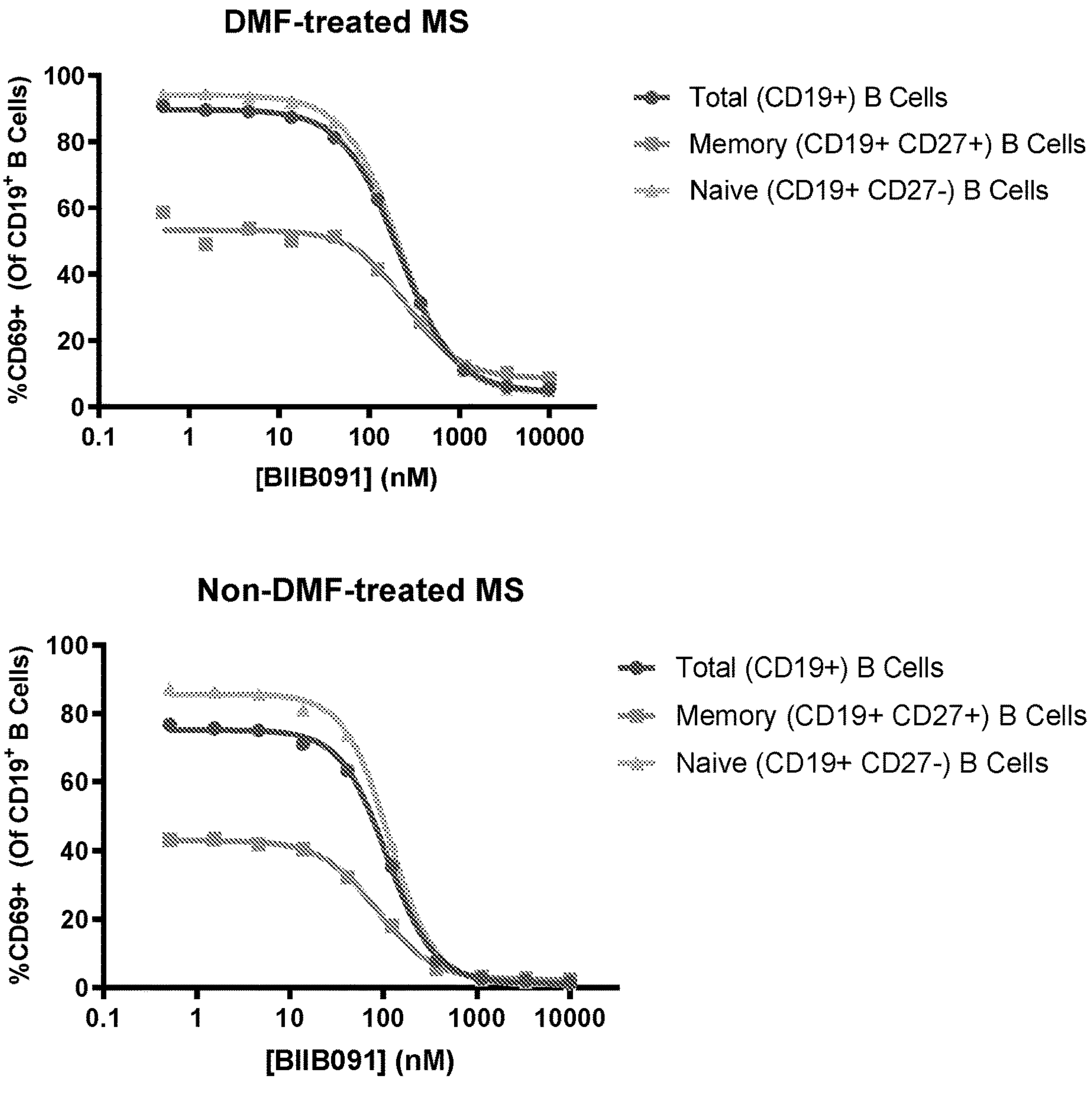
FIG. 5 shows that treatment of BIIB-091 inhibited BCR-mediated CD69 upregulation in samples from MS patients treated with DMF and MS patients not on treatment or treated with non-DMF DMTs.

As shown in FIG. 4, CD69 levels were upregulated on $CD19^+$ B cells with anti-IgD in vitro stimulation across all three patient cohorts tested. Treatment of BIIB-091 inhibited BCR-mediated CD69 upregulation in samples from MS patients treated with DMF and MS patients not on treatment or treated with non-DMF DMTs (FIG. 5).

The invention claimed is:

1. A method of treating an autoimmune disease in a subject in need thereof comprising administering to the subject an effective amount of a BTK inhibitor and an effective amount of a fumaric acid ester (FAE), wherein the BTK inhibitor is BIIB-091 and the FAE is dimethyl fumarate (DMF) or diroximel fumarate (DRF); and wherein the autoimmune disease is multiple sclerosis (MS), lupus, rheumatoid arthritis (RA), Pemphigus Vugaris (PV), neuromyelitis optica (NMO), myasthenia gravis (MG), chronic inflammatory demyelinating polyneuropathy (CIDP), anti-NMDA receptor encephalitis, or Sjögren's disease.

2. The method of claim 1, wherein the autoimmune disease is MS.

3. The method of claim 2, wherein MS is a relapsing form of MS, relapsing-remitting multiple sclerosis (RRMS), secondary progress multiple sclerosis (SPMS) or primary progressive MS (PPMS).

4. The method of claim 1, wherein the autoimmune disease is lupus.

5. The method of claim 4, wherein lupus is systemic lupus erythematosus (SLE) or cutaneous lupus erythematosus (CLE).

6. The method of claim 1, wherein the FAE is DMF.

7. The method of claim 6, wherein the FAE is DRF.

8. The method of claim 1, wherein a standard dose of the FAE is administered to the subject.

9. The method of claim 1, wherein a low dose of the FAE is administered to the subject.

* * * * *